(12) United States Patent
Haneda et al.

(10) Patent No.: US 11,959,873 B2
(45) Date of Patent: Apr. 16, 2024

(54) SENSOR USING PHENAZINE DERIVATIVE OR HIGH MOLECULAR WEIGHT REDOX POLYMER CONTAINING PHENAZINE DERIVATIVE

(71) Applicant: PHC Holdings Corporation, Tokyo (JP)

(72) Inventors: Keigo Haneda, Ehime (JP); Kazuaki Edagawa, Ehime (JP); Fumihisa Kitawaki, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 711 days.

(21) Appl. No.: 17/043,086

(22) PCT Filed: Jan. 28, 2019

(86) PCT No.: PCT/JP2019/002805
§ 371 (c)(1),
(2) Date: Sep. 29, 2020

(87) PCT Pub. No.: WO2019/187586
PCT Pub. Date: Oct. 3, 2019

(65) Prior Publication Data
US 2021/0025843 A1  Jan. 28, 2021

(30) Foreign Application Priority Data
Mar. 30, 2018  (JP) .................................. 2018-066610

(51) Int. Cl.
*G01N 27/327* (2006.01)
*A61B 5/1486* (2006.01)
*C12Q 1/00* (2006.01)

(52) U.S. Cl.
CPC ....... *G01N 27/3277* (2013.01); *A61B 5/1486* (2013.01); *C12Q 1/006* (2013.01); *G01N 27/3271* (2013.01)

(58) Field of Classification Search
CPC ... G01N 27/3277; G01N 27/327–3272; C12Q 1/006; C12Q 1/004; A61B 5/1486
See application file for complete search history.

(56) References Cited

U.S. PATENT DOCUMENTS

2005/0164329 A1* 7/2005 Wallace-Davis ....... C12Q 1/001
435/26
2006/0069211 A1   3/2006 Liu et al.
(Continued)

FOREIGN PATENT DOCUMENTS

CN      102046805      7/2013
CN      106164054      11/2016
(Continued)

OTHER PUBLICATIONS

International Search Report dated Mar. 19, 2019 in International (PCT) Application No. PCT/JP2019/002805.
(Continued)

*Primary Examiner* — Alexander S Noguerola
(74) *Attorney, Agent, or Firm* — Wenderoth, Lind & Ponack, L.L.P.

(57) ABSTRACT

The present invention forms a detection layer in an embedded biosensor probe by using a phenazine derivative as a redox mediator in which a phenazine group is covalently bonded to a high molecular weight polymer having a carboxyl group or an amino group, such as polyamino acid, polyimine, or polyallylamine; and the distance between the phenazine group and the high molecular weight polymer main chain is increased by using a polyethylene glycol chain.

4 Claims, 7 Drawing Sheets

(56) References Cited

U.S. PATENT DOCUMENTS

| | | |
|---|---|---|
| 2009/0246808 A1 | 10/2009 | Wilsey et al. |
| 2011/0290670 A1 | 12/2011 | Wilsey et al. |
| 2017/0226068 A1 | 8/2017 | Heindl et al. |
| 2021/0025843 A1 | 1/2021 | Haneda et al. |

FOREIGN PATENT DOCUMENTS

| | | |
|---|---|---|
| CN | 111936050 | 11/2020 |
| EP | 3 777 683 | 2/2021 |
| JP | 61-87676 | 5/1986 |
| JP | 10-291368 | 11/1998 |
| JP | 2006-131893 | 5/2006 |
| JP | 2011-515686 | 5/2011 |
| JP | 2013-164426 | 8/2013 |
| JP | 2014-194411 | 10/2014 |
| JP | 2016-122519 | 7/2016 |
| JP | 2017-517480 | 6/2017 |
| WO | 2018/062542 | 4/2018 |
| WO | 2019/187586 | 10/2019 |

OTHER PUBLICATIONS

International Search Report dated Dec. 3, 2019 in International (PCT) Patent Application No. PCT/JP2019/038464.
Supplementary European Search Report issued May 24, 2023 in corresponding European Application No. 19947973.4.
Winsberg et al., "TEMPO/Phenazine Combi-Molecule: A Redox-Active Material for Symmetric Aqueous Redox-Flow Batteries", ACS Energy Letter, 2016, vol. 1, pp. 976-980.

\* cited by examiner

SENSOR USING PHENAZINE DERIVATIVE OR HIGH MOLECULAR WEIGHT REDOX POLYMER CONTAINING PHENAZINE DERIVATIVE

TECHNICAL FIELD

The present disclosure relates to a sensor containing a phenazine derivative or a high molecular weight redox polymer comprising the phenazine derivative. The present disclosure relates particularly to a high molecular weight redox polymer for a biosensor using a charged redox enzyme.

BACKGROUND ART

A biosensor is a system that measures a substance by utilizing or mimicking the molecular recognition ability of a living body. An example is a measuring device that measures the amount of a specimen by using one member of a pair, such as enzyme-substrate, antigen-antibody, or hormone-receptor, as a specimen (substance to be measured) and the other member as a receptor to cause a molecular recognition reaction between the specimen and the receptor, converting a chemical change resulting from the reaction to an electrical signal with a transducer, and determining the amount of the specimen based on the intensity of the electrical signal.

In addition to the above-mentioned molecules, examples of biomolecules used for a biosensor include genes, sugar chains, lipids, peptides, cells, and tissues. In particular, biosensors using enzymes have been developed actively, and their representative example is an electrochemical glucose sensor for self-monitoring of blood glucose levels that uses an enzyme such as glucose oxidase (GOx) or glucose dehydrogenase (GDH).

In brief, the electrochemical glucose sensor for self-monitoring of blood glucose levels has a structure comprising an insulating substrate having an electrode formed on the surface thereof and a cover placed on the insulating substrate with a spacer therebetween. A reagent containing a specimen-responsive enzyme, a redox mediator (electron carrier), or the like is placed on the electrode, and this portion serves as an analyzer. A flow channel to introduce blood communicates with this analyzer at one end and is open to the outside at the other end, which serves as a blood inlet. The blood glucose level is measured by using such a sensor, for example, as follows: First, the sensor is set in a dedicated measuring device (meter). Then, a fingertip or the like is pricked with a lancet to allow for bleeding, and the blood inlet of the sensor is brought into contact with blood. The blood is drawn into the flow channel of the sensor by a capillary action, introduced into the analyzer through this flow channel, and brought into contact with the reagent. Then, a specimen-responsive enzyme E (e.g., GOx, GDH) reacts specifically with glucose in blood and oxidizes glucose. A redox mediator M accepts electrons that are generated by oxidation. The redox mediator M, which has been reduced by accepting electrons, is oxidized electrochemically on the electrode. The glucose concentration in blood, i.e., the blood glucose level is conveniently determined from an electric current value, a charge amount, or the like obtained by oxidizing the reduced redox mediator M.

Such an electrochemical blood glucose sensor plays an important role in blood glucose control for diabetes treatment, and diabetic patients can administer insulin and follow a diet appropriately on the basis of their blood glucose levels. However, patients need to measure their blood glucose level more than once per day, and collecting blood for each measurement causes pain in patients, making it difficult to maintain their quality of Life (QOL).

An embedded electrochemical glucose sensor has already been developed. The blood glucose level is continuously measured by attaching the main body 10 of such an embedded electrochemical glucose sensor 1 to a living body 2 and inserting the probe 11 into the living body (FIGS. 1 and 2). Therefore, the blood glucose level can be measured over a long time without collecting blood for each measurement.

Because the probe of the embedded biosensor is placed in the body over a long time, its components such as a specimen-responsive enzyme and a redox mediator become more likely to leach out. If the specimen-responsive enzyme or the redox mediator leaches out of the sensor, not only the detection sensitivity of the sensor is deteriorated, but the living body is also harmed. If the specimen-responsive enzyme or the redox mediator leaches out, the durability of the sensor is also degraded. Therefore, taking measures to prevent the specimen-responsive enzyme and the redox mediator from leaching out is very important.

Patent Literature 1 discloses an ionic hydrophilic high molecular weight redox polymer for an enzyme-based electrochemical sensor. In this ionic hydrophilic high molecular weight redox polymer, for example, a plurality of redox mediators are covalently bonded in a pendant-like form to a hydrophilic polymer having ionic moieties. The hydrophilic polymer is formed from hydrophilic monomers having a polymerizable acrylate or vinyl group. The redox polymer of Patent Literature 1 is obtained by covalently bonding a redox mediator, such as ferrocene, to the above-mentioned hydrophilic polymer main chain in a pendant-like form. The electrically charged redox enzyme is immobilized with an ionic bond.

CITATION LIST

Patent Literature

Patent Literature 1: JP 2006-131893 A

SUMMARY OF INVENTION

Technical Problem

It is required to prevent a redox mediator constituting a detection layer from leaching out of the probe of an embedded biosensor, in particular, to improve preservation stability (durability) while maintaining glucose detection sensitivity.

Solution to Problem

The present disclosure provides a high molecular weight redox polymer, in which a redox mediator, such as a phenazine derivative, is covalently bonded to a high molecular weight polymer, so that the redox mediator is prevented from leaching out. The redox mediator used in the present disclosure is a derivative having an amino group or a carboxyl group, and the high molecular weight polymer used in the present disclosure has a carboxyl group or an amino group. Therefore, the high molecular weight redox polymer of the present disclosure is formed with an amide bond between the amino group or the carboxyl group of the redox mediator and the carboxyl group or the amino group of the high molecular weight polymer.

Various compounds such as ferricyanides and ferrocene can be used as redox mediators. The phenazine derivative of the present disclosure is less susceptible to the effect of contaminants, such as ascorbic acid (vitamin C) and uric acid, in a biological sample because of its negative redox potential below 0 V (vs Ag/AgCl saturated KCl). Therefore, high-precision detection of a specimen (analyte) can be expected.

In the present disclosure, a phenazine derivative represented by general formula (1) can be used as a redox mediator having an amino group or a carboxyl group.

[Formula 1]

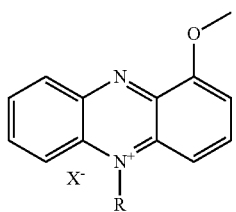

(1)

wherein $X^-$ represents an anionic species, and R represents an organic group having an amino group or a carboxyl group at an end.

Examples of the phenazine derivative represented by general formula (1) include phenazine derivatives represented by general formula (2):

[Formula 2]

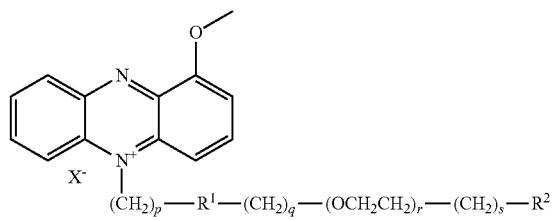

(2)

wherein $X^-$ represents an anionic species; $R^1$ does not exist or is —O—, —C(=O)—NH—, or —NH—C(=O)—; $R^2$ is —COOH or —NH$_2$ or a salt thereof; p, q, and s are each independently an integer of 1 to 15; and r is an integer of 0 to 30.

In the above formula, $X^-$, which is an anionic species, is any one selected from the group consisting of a halogen ion, an ion of a compound containing a halogen, a hydroxide ion, a carboxylate ion, a nitrate ion, a nitrite ion, an acetate ion, a hydrogen carbonate ion, a dihydrogen phosphate ion, a hydrogen sulfate ion, an alkyl sulfonate ion, a hydrogen sulfide ion, a hydrogen oxalate ion, a cyanate ion, and a thiocyanate ion or a mixture thereof.

The above-mentioned end of R or $R^2$ may be an ester of a carboxyl group and N-succinimide represented by the following formula:

[Formula 3]

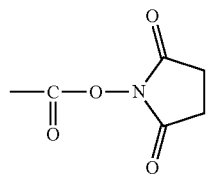

Specific examples of the phenazine derivative of the present disclosure include compounds represented by the following formula:

[Formula 4]

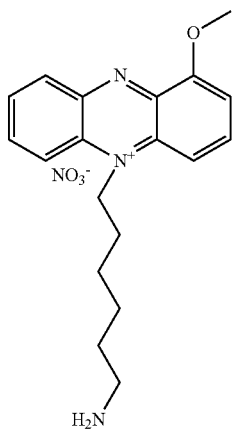

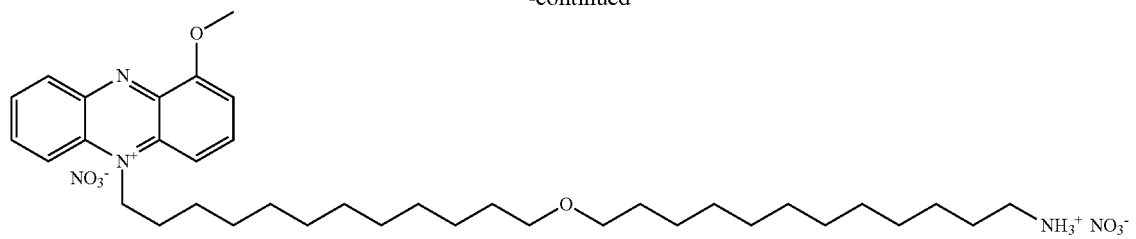

1. Phenazine Derivatives Having an Amino Group

[Formula 5]

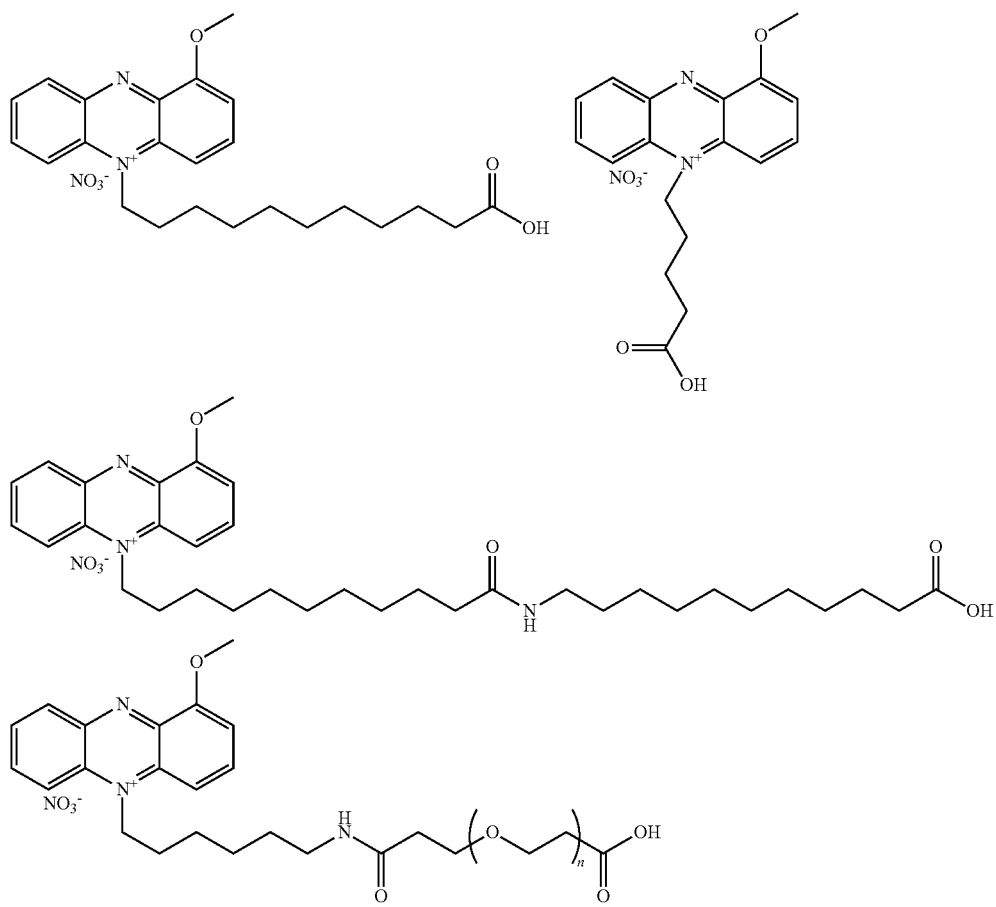

2. Phenazine Derivatives Having a Carboxyl Group wherein n represents an integer of 1 to 30.

It is preferable to increase the distance between the phenazine moiety and the high molecular weight polymer main chain with a linker, such as a polyethylene glycol chain or a hydrocarbon chain, because the thermostability of the redox mediator is improved in the biological environment.

The carboxyl group of the above-mentioned phenazine derivative having a carboxyl group may be activated by N-hydroxysuccinimide to improve its reactivity. Examples include an ester of N-hydroxysuccinimide and a phenazine derivative represented by the following formula:

[Formula 6]

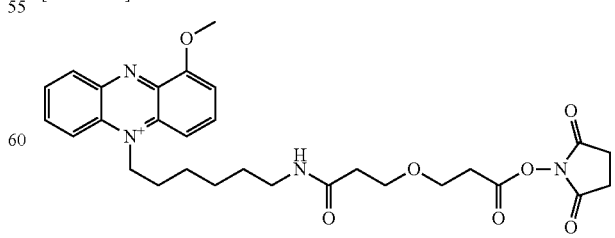

All the above-mentioned phenazine derivatives having a carboxyl group form an ester with N-hydroxysuccinimide.

In the present disclosure, for example, a polymer formed from the following polyamino acids, polyimine, and polymerizable acrylate or a vinyl group can be used as a high molecular weight polymer having a carboxyl group or an amino group:

[Formula 7]

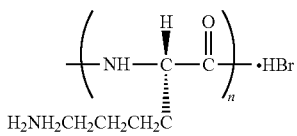

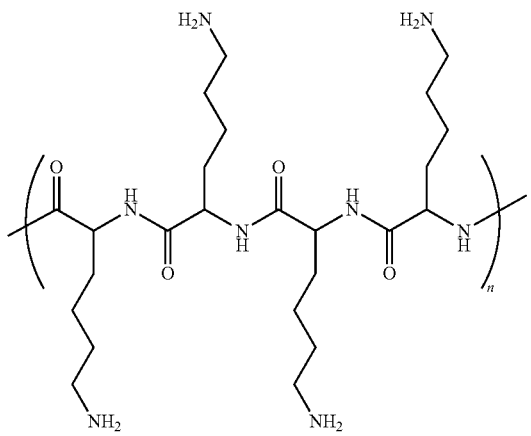

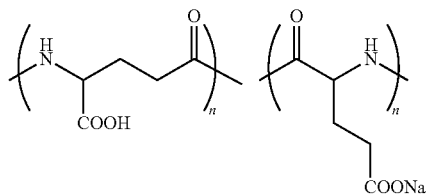

1. Polyamino Acids Having an Amino Group

[Formula 8]

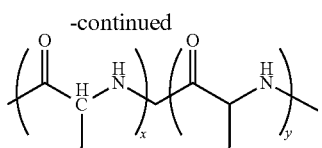

-continued

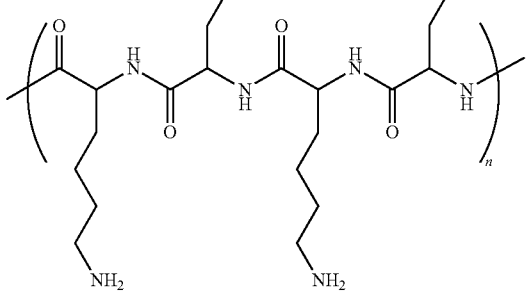

2. Polyamino Acids Having a Carboxyl Group

[Formula 9]

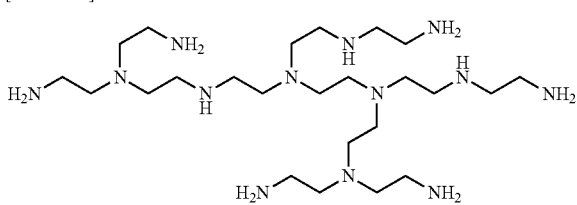

3. Polyimine Having an Amino Group

[Formula 10]

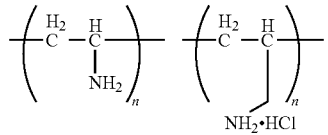

4. Polyvinyls Having an Amino Group

The high molecular weight redox polymer of the present disclosure is formed with an amide bond between a phenazine derivative having an amino group and a high molecular weight polymer having a carboxyl group or an amide bond between a phenazine derivative having a carboxyl group and a high molecular weight polymer having an amino group.

An electrically charged redox enzyme can be further bonded covalently to the high molecular weight redox polymer of the present disclosure directly with an amide bond similar to those mentioned above or via a linker, such as a polyethylene glycol chain or a hydrocarbon chain.

5. Proteins

In the present disclosure, proteins such as, for example, bovine serum albumin (BSA), glucose dehydrogenase (GDH), and glucose oxidase (GOx) can be used as the high molecular weight polymer having a carboxyl group or an amino group. That is, examples of the high molecular weight redox polymer of the present disclosure also include a complex in which a phenazine derivative binds to an electrically charged redox enzyme.

An example of the internal structure of a probe of an embedded biosensor using the high molecular weight redox polymer of the present disclosure is shown in FIGS. 3 to 6, but this structure is exemplary and does not limit the scope of application of the high molecular weight redox polymer of the present disclosure.

An embedded biosensor 1 comprises a main body 10 and a probe 11. In brief, the probe 11 has a key shape consisting of a sensing portion inserted into the living body and a terminal portion to be electrically connected to the internal circuit of the biosensor main body 10. The sensing portion is formed thinly so as to be inserted into the body, and the terminal portion has a specific size so as to be inserted into the biosensor main body 10 to form an electric connection. Therefore, the insulating substrate 111 of a key shape is first prepared.

FIG. 3 shows a top view viewed from the front side, and FIG. 4 shows a cross-sectional view by a cutting plane line A-A' in FIG. 3.

A conductive thin film 112 is formed by depositing carbon or a conductive metal material selected from the group consisting of metals such as gold, silver, platinum, and palladium on both sides of the insulating substrate 111 by sputtering, vapor deposition, ion plating, or the like.

A groove 113 of a depth to reach the surface of the insulating substrate 111 is formed by laser lithography in the conductive thin film 112 formed on the front side of the insulating substrate 111 to separate and electrically insulate a working electrode lead 112a and a reference electrode lead 112b.

Insulating resist films 116a, 116b having an opening at a prespecified position are formed on both sides of the insulating substrate 111.

Ag/AgCl is deposited at an opening for a reference electrode of the resist film 116a formed on the front side of the insulating substrate 111 by a screen printing method or an ink-jet printing method to form the reference electrode 115.

A detection layer 118 containing conductive particles, a specimen-responsive enzyme, and a redox mediator is formed by coating and drying a suspension of conductive particles such as carbon particles, an aqueous solution of the high molecular weight redox polymer in which the redox mediator is covalently bonded, an aqueous solution of the specimen-responsive enzyme, and the like on the working electrode 114. The specimen-responsive enzyme may also be covalently bonded to this high molecular weight redox polymer.

In the present disclosure, a "specimen-responsive enzyme" means a biochemical substance that can specifically catalyzes oxidation or reduction of a specimen. The specimen-responsive enzyme may be any biochemical substance as long as it can be used in a biosensor for the purpose of detection. When glucose is a specimen, examples of suitable specimen-responsive enzymes include glucose oxidase (GOx) and glucose dehydrogenase (GDH). A "redox mediator" means an oxidizing/reducing substance that mediates electron transfer and is responsible for electron transfer caused by redox reaction of a specimen (analyte) in a biosensor. Examples include but not limited to phenazine derivatives, and the redox mediator may be any oxidizing/reducing substance as long as it can be used in a biosensor for the purpose of detection.

A protective film 119 can be formed on both faces and side faces and at ends of the sensing portion by immersing the sensing portion in a solution containing a polymer for the protective film.

Advantageous Effects of Invention

The high molecular weight redox polymer of the present disclosure can prevent a redox mediator from leaching out when the high molecular weight redox polymer is used for the probe of an embedded biosensor because the redox polymer is covalently bonded to the high molecular weight polymer. The high molecular weight redox polymer of the present disclosure can prevent not only deterioration of detection sensitivity, but also a harm to the living body.

DESCRIPTION OF EMBODIMENTS

Figure 1:
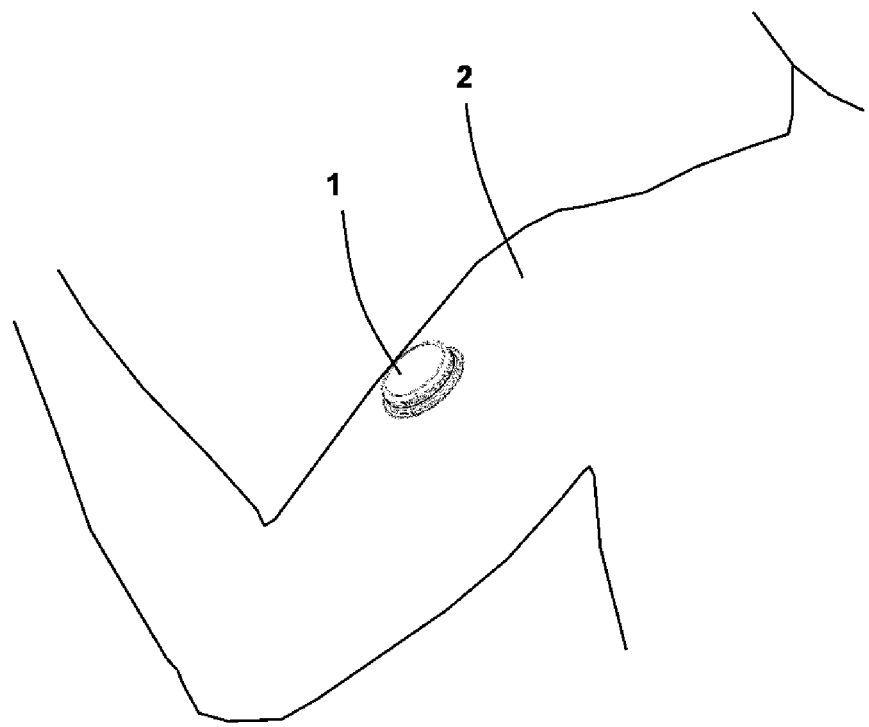
FIG. 1 is a schematic view showing an embedded biosensor attached to a living body (human body).
Figure 2:
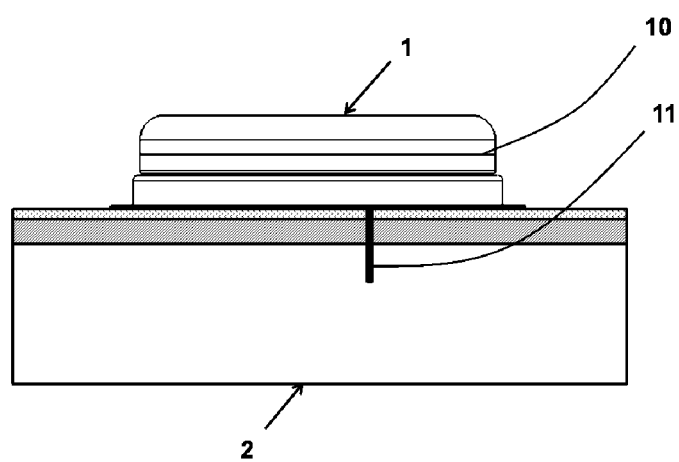
FIG. 2 is a cross-sectional view showing the embedded biosensor in the state of being attached to the living body (human body).
Figure 3:
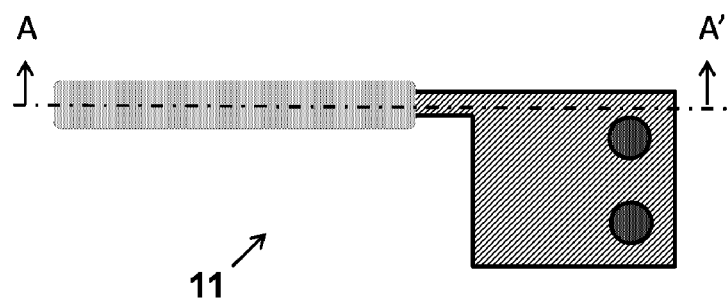
FIG. 3 is a top view showing the front side of the probe of an embedded biosensor which is a specific example of the present disclosure.
Figure 4:
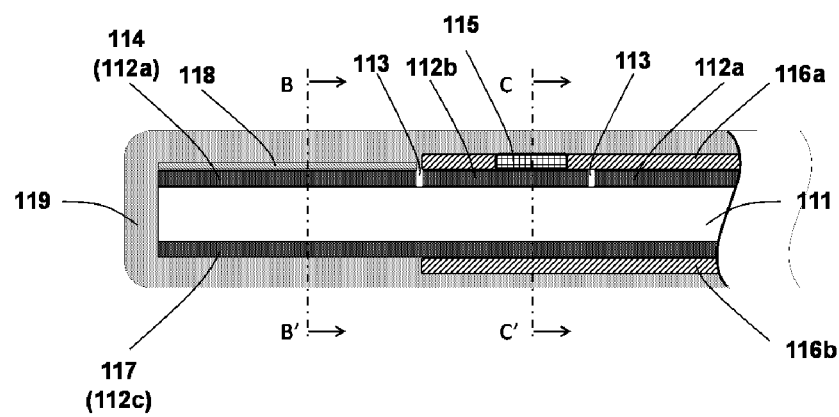
FIG. 4 is a cross-sectional view by the A-A' cutting plane line in FIG. 3.
Figure 5:
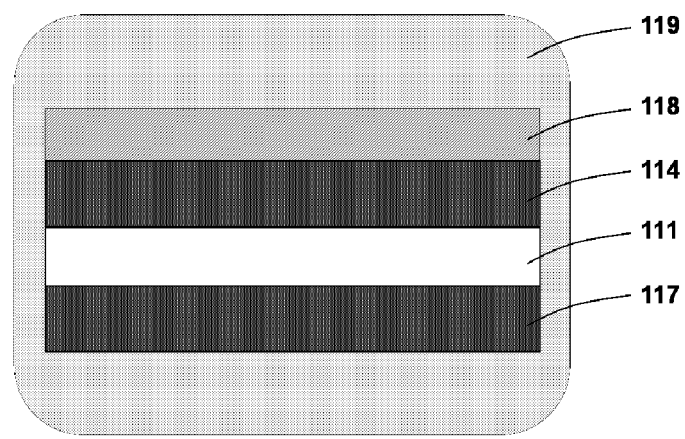
FIG. 5 is a cross-sectional view by the B-B' cutting plane line in FIG. 4.
Figure 6:
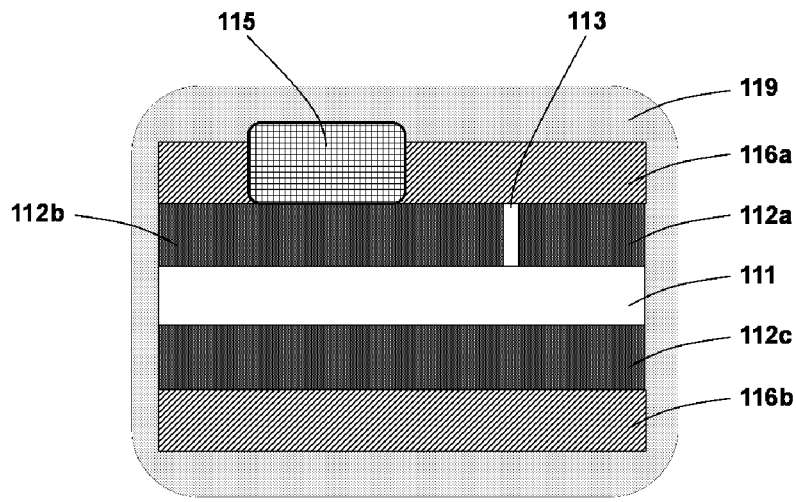
FIG. 6 is a cross-sectional view by the C-C' cutting plane line in FIG. 4.

A. Synthesis of a Low Molecular Weight Phenazine Derivative

In brief, the above-mentioned phenazine derivative having an amino group or a carboxyl group can be synthesized by the following synthesis schemes.

Synthesis Example 1: Synthesis of a Phenazine Derivative Having an Amino Group

For example, 5-(6-aminohexyl)-1-methoxyphenazinium nitrate is synthesized by allowing an N-alkylating agent to act on 1-methoxyphenazine to synthesize 5-[6-(N-phthalimide)hexyl]-1-methoxyphenazinium nitrate and then removing phthalimide. A desired N-alkylaminophenazinium salt can be synthesized by selecting a corresponding N-alkylating agent.

[Formula 11]

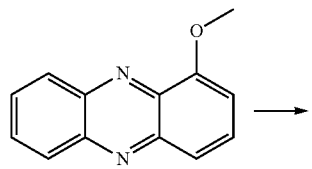

Synthesis Example 2: Synthesis of a Phenazine Derivative Having an Amino Group Similarly, for example, 5-{12-[(12-ammoniododecyl)oxy]dodecyl}-1-methoxyphenazin-5-ium dinitrate is synthesized by allowing an N-alkylating agent to act on 1-methoxyphenazine.

[Formula 12]

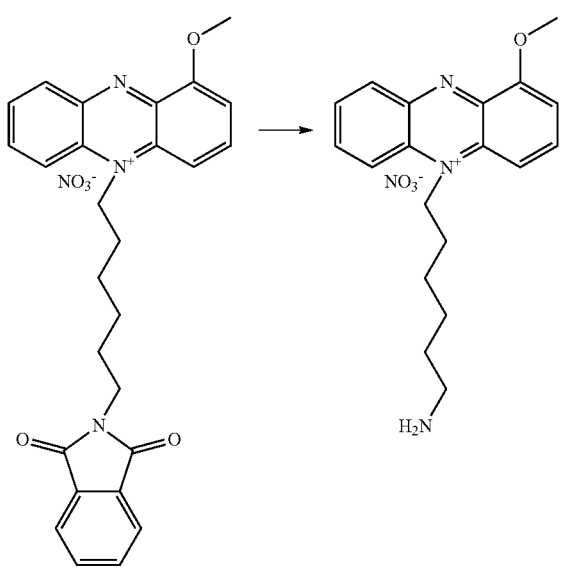

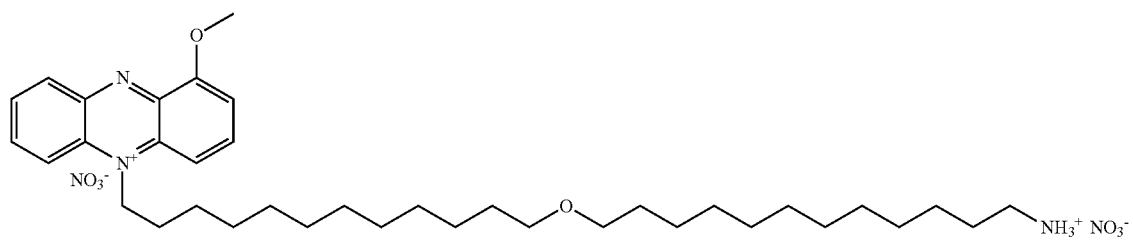

Synthesis Example 3: Synthesis of a Phenazine Derivative Having a Carboxyl Group For example, 5-(4-carboxybutyl)-1-methoxyphenazinium nitrate is synthesized by allowing an N-alkylating agent to act on 1-methoxyphenazine. Further, 5-{[(2,5-dioxopyridin-1-yl)oxy]-5-oxopentyl}-1-methoxyphenazinium nitrate is synthesized in which N-hydroxysuccinimide has been added to a carboxyl group at an end to improve the reactivity of the carboxyl group. A desired N-alkylcarboxyphenazinium salt can be synthesized by selecting a corresponding N-alkylating agent.

[Formula 13]

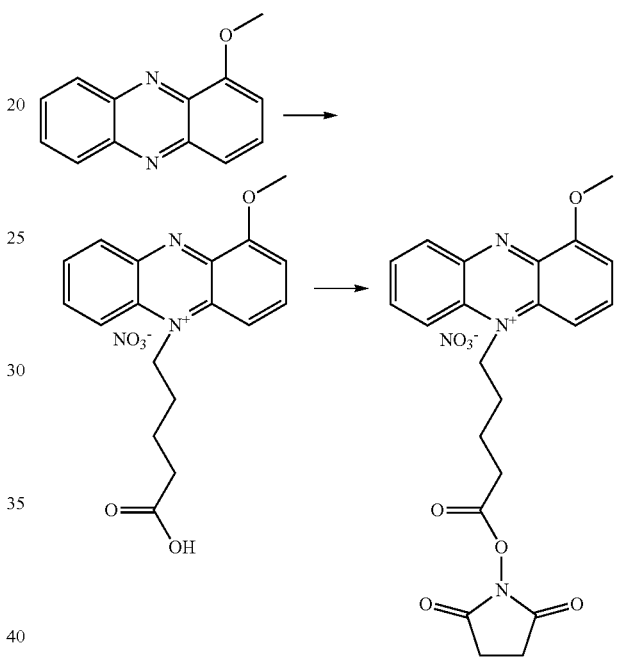

Synthesis Example 4: Synthesis of a Phenazine Derivative Having a Carboxyl Group Similarly, 5-{11-[(2,5-dioxopyrrolidin-1-yl)oxy]-11-oxoundecyl}-1-methoxyphenazin-5-ium nitrate is synthesized by allowing an N-alkylating agent to act on 1-methoxyphenazine and further by adding N-hydroxysuccinimide a carboxyl group at an end to improve the reactivity of the carboxyl group.

[Formula 14]

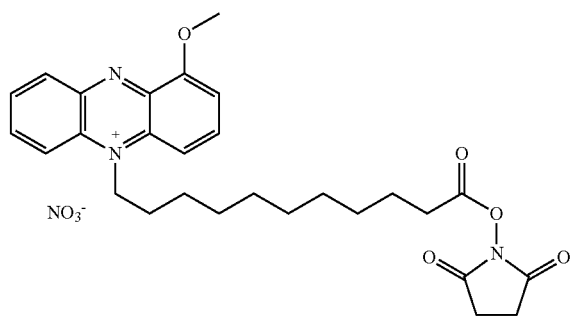

Synthesis Example 5: Synthesis of a Phenazine Derivative Having a Carboxyl Group Similarly, 5-{11-[11-(2,5-dioxopyrrolidin-1-yloxy)-11-oxoundecylamino]-11-oxoundecyl}-1-methoxyphenazin-5-ium nitrate is synthesized by allowing an N-alkylating agent to act on 1-methoxyphenazine and further by adding N-hydroxysuccinimide to a carboxyl group at an end to improve the reactivity of the carboxyl group.

[Formula 15]

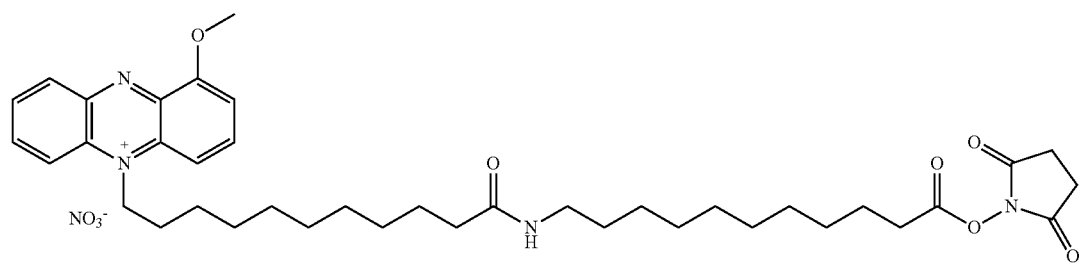

B. Synthesis of a High Molecular Weight Redox Polymer in which a Phenazine Derivative is Covalently Bonded A high molecular weight redox polymer can be synthesized by covalently bonding any of the phenazine derivatives synthesized in Synthesis Examples 1 to 5 or various phenazine derivatives synthesized according to the above-described Synthesis Examples to a high molecular weight polymer having a carboxyl group or an amino group.

Example 1

6.47 mg of 5-{12-[(12-ammoniododecyl)oxy]dodecyl}-1-methoxyphenazin-5-ium dinitrate (Ph-C24-NH$_3^+$) obtained in Synthesis Example 2:

[Formula 16]

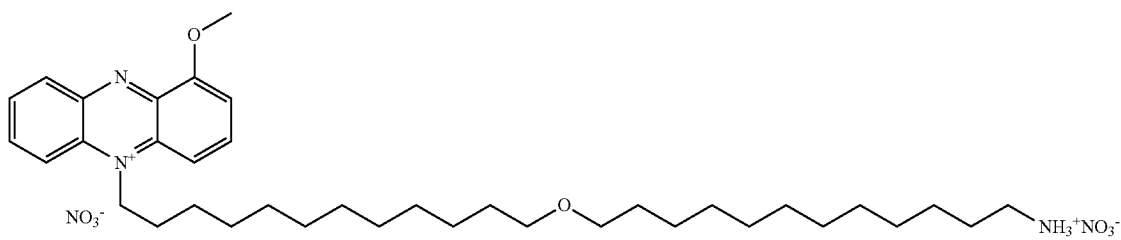

was weighed and dissolved in 500 μL of ethanol. Separately, 11.86 mg of poly(L-sodium glutamate) (Peptide Institute, Inc.; Code 3063; M.W.>12,000, cutoff of by dialysis) represented by general formula:

[Formula 17]

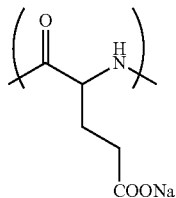

was weighed and dissolved in 1.5 mL of 100 mM 2-morpholinoethanesulfonic acid (MES) buffer solution (pH 6.0). Separately, 8.8 mg of water-soluble carbodiimide (WSC) (Dojindo Laboratories) was weighed and dissolved in 500 μL of 100 mM MES buffer solution (pH 6.0). The above-described three solutions were mixed and allowed to react with stirring at room temperature for 4 hours.

The reaction solution was subjected to gel filtration chromatography using PD-10 Column (GE Healthcare) with phosphate buffered saline (PBS, pH 7.4) as an elution buffer. After gel filtration, the solution was ultrafiltered using a centrifugal ultrafiltration filter (Amicon Ultra-4 10k; Merck Millipore). A high molecular weight polymer (PGA-C24-Ph) in which phenazine is covalently bonded to poly(L-sodium glutamate) was obtained by the above-described procedure.

A solution of the obtained PGA-C24-Ph was adjusted with PBS to have an absorbance of approximately 11 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 2

0.70 mg of 5-{11-[(2,5-dioxopyrrolidin-1-yl)oxy]-11-oxoundecyl}-1-methoxyphenazin-5-ium nitrate (Ph-C11-Su) obtained in Synthesis Example 4:

[Formula 18]

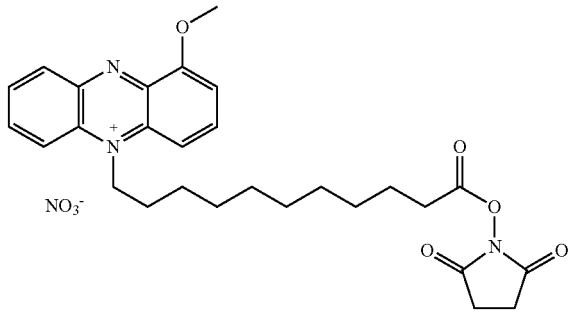

was weighed and dissolved in 500 μL of 100 mM 2-morpholinoethanesulfonic acid (MES) buffer solution (pH 6.0). Separately, 3.34 mg of poly(L-lysine) hydrochloride (Peptide Institute, Inc.; Code 3075; M.W.>12,000; cutoff of by dialysis) represented by general formula:

[Formula 19]

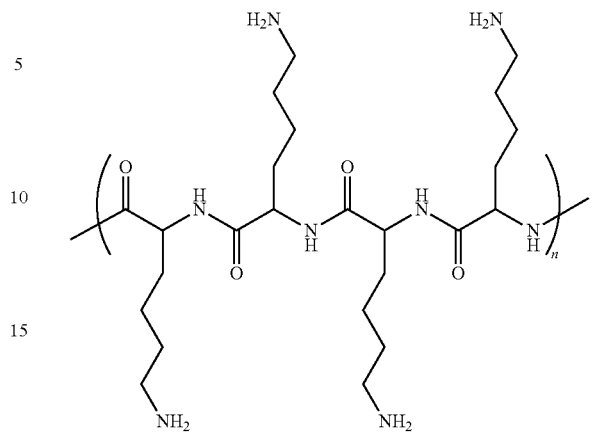

was weighed and was dissolved in 500 μL of 100 mM MES buffer solution (pH 6.0). The above-described two solutions were mixed and allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore). A high molecular weight polymer (PLL-C11-Ph) in which phenazine is covalently bonded to poly(L-lysine) hydrochloride was obtained by the above-described procedure.

A solution of the obtained PLL-C11-Ph was adjusted with PBS to have an absorbance of approximately 11 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 3

0.6 mg of 5-{[(2,5-dioxopyridin-1-yl)oxy]-5-oxopentyl}-1-methoxyphenazinium nitrate (Ph-C5-Su) obtained in Synthesis Example 3:

[Formula 20]

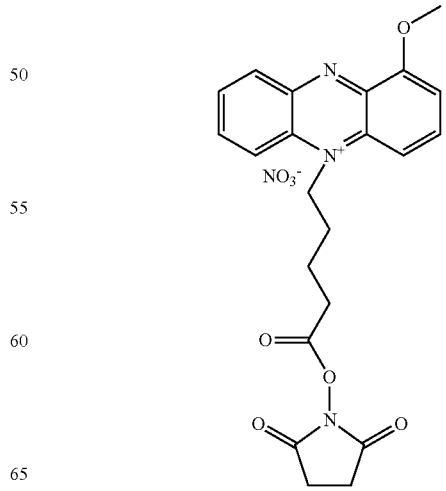

was weighed and dissolved in 120 µL of 100 mM 2-morpholinoethanesulfonic acid (MES) buffer solution (pH 6.0). Separately, 5 mg of poly(L-lysine) hydrochloride (Peptide Institute, Inc.; Code 3075; M.W.>12,000; cutoff of by dialysis) was weighed and dissolved in 1 mL of 100 mM MES buffer solution (pH 6.0). The above-described two solutions were mixed and allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight polymer (PLL-C5-Ph 1) in which phenazine is covalently bonded to poly(L-lysine) hydrochloride was obtained by the above-described procedure.

A solution of the obtained PLL-C5-Ph 1 was adjusted with PBS to have an absorbance of approximately 11 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 4

2 mg of Ph-C5-Su obtained in Synthesis Example 3 was weighed and dissolved in 500 µL of 100 mM 2-morpholinoethanesulfonic acid (MES) buffer solution (pH 6.0). Separately, 3.31 mg of polyallylamine hydrochloride (Sigma-Aldrich; Product Number 283215; weight-average molecular weight (PEG equivalent) by GPC measurement Mw≈17,500) represented by general formula:

[Formula 21]

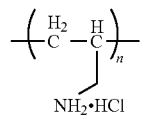

was weighed and dissolved in 500 µL of 100 mM MES buffer solution (pH 6.0). The above-described two solutions were mixed and allowed to react with stirring at room temperature for 4 hours.

The reaction solution was subjected to gel filtration chromatography using PD-10 Column (GE Healthcare) with 10 mM sodium phosphate buffer solution (pH 6.5) as an elution buffer. After gel filtration, the solution was ultrafiltered using a centrifugal ultrafiltration filter (Amicon Ultra-4 10k; Merck Millipore).

A high molecular weight polymer (PAA-C5-Ph) in which phenazine is covalently bonded to polyallylamine hydrochloride was obtained by the above-described procedure.

A solution of the obtained PAA-C5-Ph was adjusted with a sodium phosphate buffer solution (pH 6.5) to have an absorbance of approximately 11 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of 10 mM sodium phosphate buffer solution (pH 6.5) as a blank value.

Example 5

2.38 mg of Ph-C5-Su obtained in Synthesis Example 3 was weighed and dissolved in 1 mL of 100 mM 2-morpholinoethanesulfonic acid (MES) buffer solution (pH 6.0). Separately, 5 mg of poly(ethylene imine) solution (Sigma-Aldrich; Product Number 181978; number-average molecular weight by GPC measurement Mn≈60,000; weight-average molecular weight by LS measurement Mw≈750,000; 50% by weight in H₂O) represented by general formula:

[Formula 22]

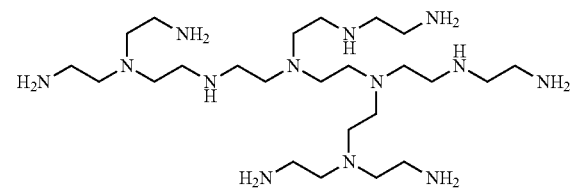

was weighed and dissolved in 1.5 mL of 100 mM MES buffer solution (pH 6.0). The above-described two solutions were mixed and allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight polymer (PEI-C5-Ph) in which phenazine is covalently bonded to polyethyleneimine was obtained by the above-described procedure.

A solution of the obtained PEI-C5-Ph was adjusted with PBS to have an absorbance of approximately 11 at 386 nm with measuring in a microplate (Greiner Bio-One; UV-STAR MICROPALLETE 96 WELL F-BODE) using a plate reader (TECAN; Infinite M200 PRO). The absorbance was obtained by reducing the measured absorbance of PBS as a blank value.

Example 6

0.91 mg Ph-C5-Su obtained in Synthesis Example 3 was weighed and dissolved in 1 mL of 100 mM 2-morpholinoethanesulfonic acid (MES) buffer solution (pH 6.0). Separately, 8.75 mg of an aqueous solution of an allylamine hydrochloride-diallylamine hydrochloride copolymer (Nittobo Medical Co., Ltd.; PAA-D11-HCL; weight-average molecular weight Mw=100,000; concentration 40%; pH (5% sol) 2-3; viscosity 600 mPa·s) represented by general formula:

[Formula 23]

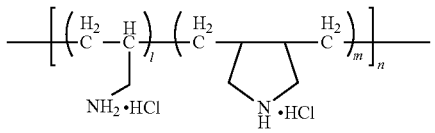

was weighed and dissolved in 1.5 mL of 100 mM MES buffer solution (pH 6.0). The above-described two solutions were mixed and allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight polymer (PAA-DAA-C5-Ph) in which phenazine is covalently bonded to an allylamine hydrochloride-diallylamine hydrochloride copolymer was obtained by the above-described procedure.

A solution of the obtained PAA-DAA-C5-Ph was adjusted with PBS to have an absorbance of approximately 11 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 7

2.04 mg of Ph-C5-Su obtained in Synthesis Example 3 was weighed and dissolved in 1 mL of 100 mM 2-morpholinoethanesulfonic acid (MES) buffer solution (pH 6.0). Separately, 6.88 mg of an aqueous solution of an allylamine-diallyldimethylammonium chloride copolymer (Nittobo Medical Co., Ltd.; PAA-1123; weight-average molecular weight Mw=18,000; concentration 15%; pH (5% sol) 11, viscosity 14 mPa·s) represented by general formula:

[Formula 24]

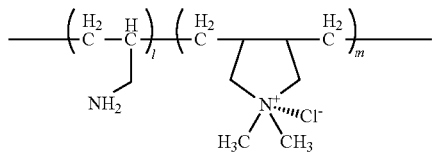

was weighed and dissolved in 1.5 mL of 100 mM MES buffer solution (pH 6.0). The above-described two solutions were mixed and allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 10k; Merck Millipore).

A high molecular weight polymer (PAA-DADMA-C5-Ph) in which phenazine is covalently bonded to an allylamine-diallyldimethylammonium chloride copolymer was obtained by the above-described procedure.

A solution of the obtained PAA-DADMA-C5-Ph was adjusted with PBS to have an absorbance of approximately 11 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 8

0.43 mg of Ph-C5-Su obtained in Synthesis Example 3 was weighed and dissolved in 300 µL of 100 mM 4-(2-hydroxyethyl)-1-piperazineethanesulfonic acid (HEPES) buffer solution (pH 7.0). Separately, 0.6 mg of bovine serum albumin (BSA) (Nakalai Tesque; Product Code 01860-65; General Grade; pH 7.0) was weighed and was dissolved in 200 µL of 100 mM HEPES buffer solution (pH 7.0). The above-described two solutions were mixed and allowed to react with stirring at room temperature for 4 hours.

The reaction solution was subjected to gel filtration chromatography using PD MiniTrap G-25 Column (GE Healthcare) with PBS as an elution buffer. After gel filtration, the solution was ultrafiltered using a centrifugal ultrafiltration filter (Amicon Ultra-4 30k; Merck Millipore).

A protein (BSA-C5-Ph) in which phenazine is covalently bonded to BSA was obtained by the above-described procedure.

A solution of the obtained BSA-C5-Ph was adjusted with PBS to have an absorbance of approximately 11 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 9

0.86 mg of Ph-C5-Su obtained in Synthesis Example 3 was weighed and dissolved in 300 µL of 100 mM HEPES buffer solution (pH 7.0). Separately, 1.37 mg of glucose dehydrogenase (FAD-dependent) (BBI International; GDH GLD1) was weighed and dissolved in 200 µL of 100 mM HEPES buffer solution (pH 7.0). The above-described two solutions were mixed and allowed to react with stirring at room temperature for 4 hours.

The reaction solution was subjected to gel filtration chromatography using PD MiniTrap G-25 Column (GE Healthcare) with PBS as an elution buffer. After gel filtration, the solution was ultrafiltered using a centrifugal ultrafiltration filter (Amicon Ultra-4 30k; Merck Millipore).

A protein (GDH-C5-Ph) in which phenazine is covalently bonded to glucose dehydrogenase was obtained by the above-described procedure.

A solution of the obtained GDH-C5-Ph was adjusted with PBS to have an absorbance of approximately 11 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 10

2.78 mg of 5-{11-[11-(2,5-dioxopyrrolidin-1-yloxy)-11-oxoundecylamino]-11-oxoundecyl}-1-methoxyphenazin-5-ium nitrate (Ph-C22-Su) obtained in Synthesis Example 5 was weighed and dissolved in 500 µL of ethanol. Separately, 15 mg of glucose dehydrogenase (FAD-dependent) (BBI International; GDH GLD1) was weighed and dissolved in 2 mL of 100 mM HEPES buffer solution (pH 7.0). The above-described two solutions were mixed and allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A protein (GDH-C22-Ph) in which phenazine is covalently bonded to glucose dehydrogenase was obtained by the above-described procedure.

A solution of the obtained GDH-C22-Ph was adjusted with PBS to have an absorbance of approximately 11 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Comparative Example 1

0.63 mg of 5-(6-aminohexyl)-1-methoxyphenazinium nitrate (Ph-C6-NH2) obtained in Synthesis Example 1 represented by the following formula:

[Formula 25]

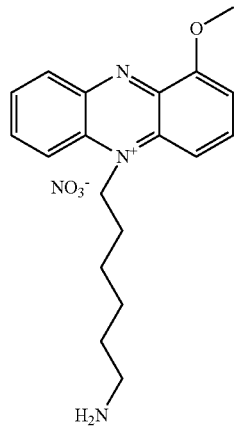

was weighed and dissolved in 500 µL of PBS to obtain a Ph-C6-NH2 solution.

When the obtained solution was measured in a microplate (Greiner Bio-One; UV-STAR MICROPALLETE 96 WELL F-BODEN) using a plate reader (TECAN; Infinite M200 PRO), the absorbance at 386 nm was approximately 11. The absorbance was obtained by reducing the measured absorbance of PBS as a blank value.

Example 11

2 mg of Ph-C5-Su obtained in Synthesis Example 3 was weighed and dissolved in 500 µL of 100 mM MES buffer solution (pH 6.0). Separately, 11.33 mg of poly(L-lysine) hydrochloride (Peptide Institute, Inc.; Code 3075; M.W.>12,000, cutoff of by dialysis) was weighed and dissolved in 500 µL of 100 mM MES buffer solution (pH 6.0). The above-described two solutions were mixed and allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight polymer (PLL-C5-Ph 2) in which phenazine is covalently bonded to poly(L-lysine) hydrochloride was obtained by the above-described procedure.

A solution of the obtained PLL-C5-Ph 2 was adjusted with PBS to have an absorbance in the range of 0.52 to 0.57 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 12

2 mg of Ph-C6-NH2 obtained in Synthesis Example 1 was weighed and dissolved in 300 µL of 100 mM MES buffer solution (pH 6.0). Separately, 1.8 mg of Acid-PEGS-NHS ester (BroadPharm) was weighed and dissolved in 300 µL of 100 mM MES buffer solution (pH 6.0). The above-described two solutions were mixed and allowed to react with stirring at room temperature for approximately 20 hours to obtain Solution A containing PEG chain-bonded phenazinium nitrate represented by the following formula:

[Formula 26]

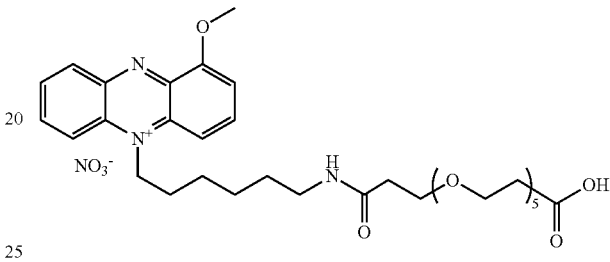

Separately, 11.02 mg of poly(L-lysine) hydrochloride (Peptide Institute, Inc.; Code 3075; M.W.>12,000, cutoff of by dialysis) was weighed and dissolved in 300 µL of 100 mM MES buffer solution (pH 6.0). Separately, 4 mg of water-soluble carbodiimide (WSC) (Dojindo Laboratories) was weighed and dissolved in 100 µL of 100 mM MES buffer solution (pH 6.0). The above-mentioned poly(L-lysine) hydrochloride and WSC solution were mixed sequentially into Solution A, and the mixture was allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight polymer (PLL-PEGS-Ph) in which phenazine is covalently bonded to poly(L-lysine) hydrochloride grafted with a polyethylene glycol (PEG) chain comprising 5 units of ethylene glycol was obtained by the above-described procedure.

A solution of the obtained PLL-PEGS-Ph was adjusted with PBS to have an absorbance in the range of 0.52 to 0.57 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 13

2 mg of Ph-C6-NH2 obtained in Synthesis Example 1 was weighed and dissolved in 300 µL of 100 mM MES buffer solution (pH 6.0). Separately, 3.26 mg of Acid-PEG13-NHS ester (BroadPharm) was weighed and dissolved in 300 µL of 100 mM MES buffer solution (pH 6.0). The above-described two solutions were mixed, and the mixture was allowed to react at room temperature for approximately 20 hours to obtain Solution B containing PEG chain-bonded *phenazinium* nitrate represented by the following formula:

[Formula 27]

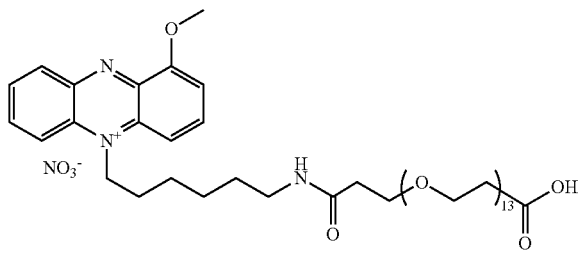

Separately, 11.02 mg of poly(L-lysine) hydrochloride (Peptide Institute, Inc.; Code 3075; M.W.>12,000, cutoff of by dialysis) was weighed and dissolved in 300 μL of 100 mM MES buffer solution (pH 6.0). Separately, 4 mg of water-soluble carbodiimide (WSC) (Dojindo Laboratories) was weighed and dissolved in 100 μL of 100 mM MES buffer solution (pH 6.0). The above-mentioned poly(L-lysine) hydrochloride and WSC solution were mixed sequentially into Solution B, and the mixture was allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight polymer (PLL-PEG13-Ph) in which phenazine is covalently bonded to poly(L-lysine) hydrochloride grafted with a polyethylene glycol (PEG) chain comprising 13 units of ethylene glycol was obtained by the above-described procedure.

A solution of the obtained PLL-PEG13-Ph was adjusted with PBS to have an absorbance in the range of 0.52 to 0.57 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

Example 14

2 mg of Ph-C6-NH2 obtained in Synthesis Example 1 was weighed and dissolved in 300 μL of 100 mM MES buffer solution (pH 6.0). Separately, 5.44 mg of Acid-PEG25-NHS ester (BroadPharm) was weighed and dissolved in 300 μL of 100 mM MES buffer solution (pH 6.0). The above-described two solutions were mixed, and the mixture was allowed to react with stirring at room temperature for approximately 20 hours to obtain Solution C containing PEG chain-bonded phenazinium nitrate represented by the following formula:

[Formula 28]

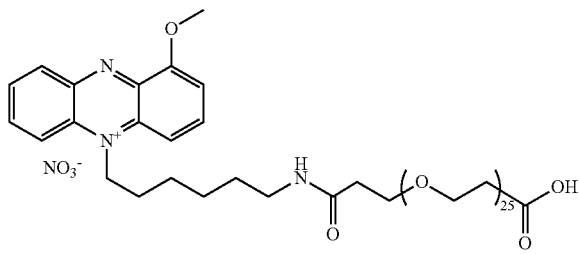

Separately, 11.02 mg of poly(L-lysine) hydrochloride (Peptide Institute, Inc.; Code 3075; M.W.>12,000, cutoff of by dialysis) was weighed and dissolved in 300 μL of 100 mM MES buffer solution (pH 6.0). Separately, 4 mg of water-soluble carbodiimide (WSC) (Dojindo Laboratories) was weighed and dissolved in 100 μL of 100 mM MES buffer solution (pH 6.0). The above-mentioned poly(L-lysine) hydrochloride and WSC solution were mixed sequentially into Solution C, and the mixture was allowed to react with stirring at room temperature for 4 hours.

The reaction solution was subjected to gel filtration chromatography using PD-10 Column (GE Healthcare) with PBS as an elution buffer. After gel filtration, the solution was ultrafiltered using a centrifugal ultrafiltration filter (Amicon Ultra-4 30k; Merck Millipore).

A high molecular weight polymer (PLL-PEG25-Ph) in which phenazine is covalently bonded to poly(L-lysine) hydrochloride grafted with a polyethylene glycol (PEG) chain comprising 25 units of ethylene glycol was obtained by the above-described procedure.

A solution of the obtained PLL-PEG25-Ph was adjusted with PBS to have an absorbance in the range of 0.52 to 0.57 at 386 nm with measuring in a microplate (Greiner Bio-One; UV-STAR MICROPALLETE 96 WELL F-BODEN) using a plate reader (TECAN; Infinite M200 PRO). The absorbance was obtained by reducing the measured absorbance of PBS as a blank value.

C. Evaluation Tests (1) Leaching of Mediators

Cyclic voltammetry was performed at a sweep rate of 10 mV/s using a potentionstat (BAS Inc.) with three electrodes comprising gold electrodes as a working electrode and a counter electrode and an Ag/AgCl (saturated potassium chloride) (BAS Inc.) as a reference electrode.

10 μL each of solutions of various phenazine derivative-bonded high molecular weight redox polymers obtained in Examples 1 to 7 was applied on the working electrode and dried.

0.6 μL of a ketjen black suspension was applied on the working electrode and dried for approximately 10 minutes. Then, 0.6 μL each of solutions of various phenazine derivative-bonded proteins obtained in Examples 8 to 10 was applied and dried for approximately one hour.

In a volume of 10 μL of a solution of Ph-C6-NH2 obtained in Comparative Example 1 was applied on the working electrode and dried.

Figure 7:
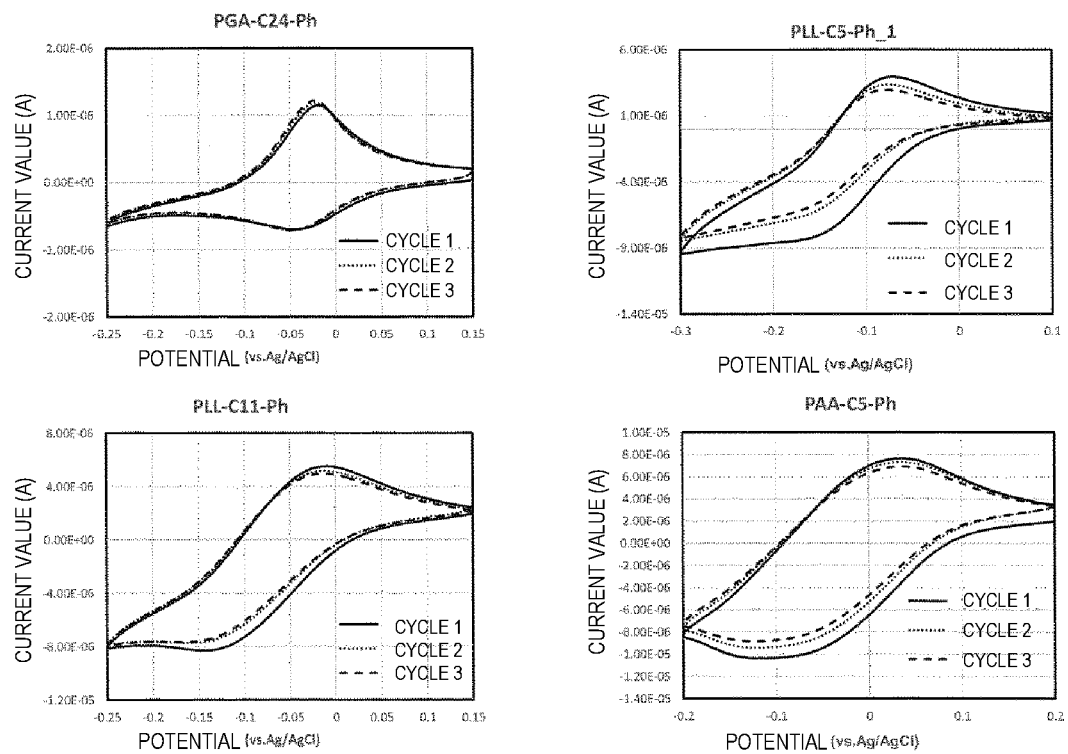
FIG. 7 is a voltammogram of the sensor of the present disclosure using a high molecular weight polymer to which a phenazine derivative is covalent bonded.
Figure 8:
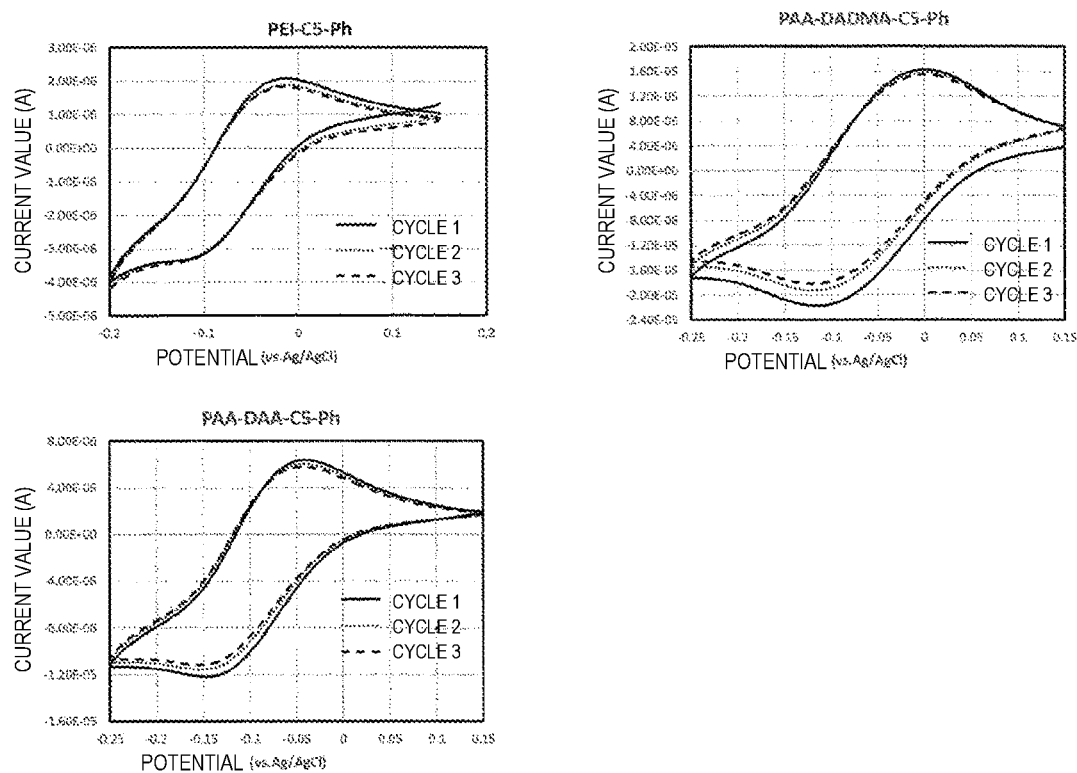
FIG. 8 is a voltammogram of the sensor of the present disclosure using a high molecular weight polymer to which a phenazine derivative is covalently bonded.
Figure 9:
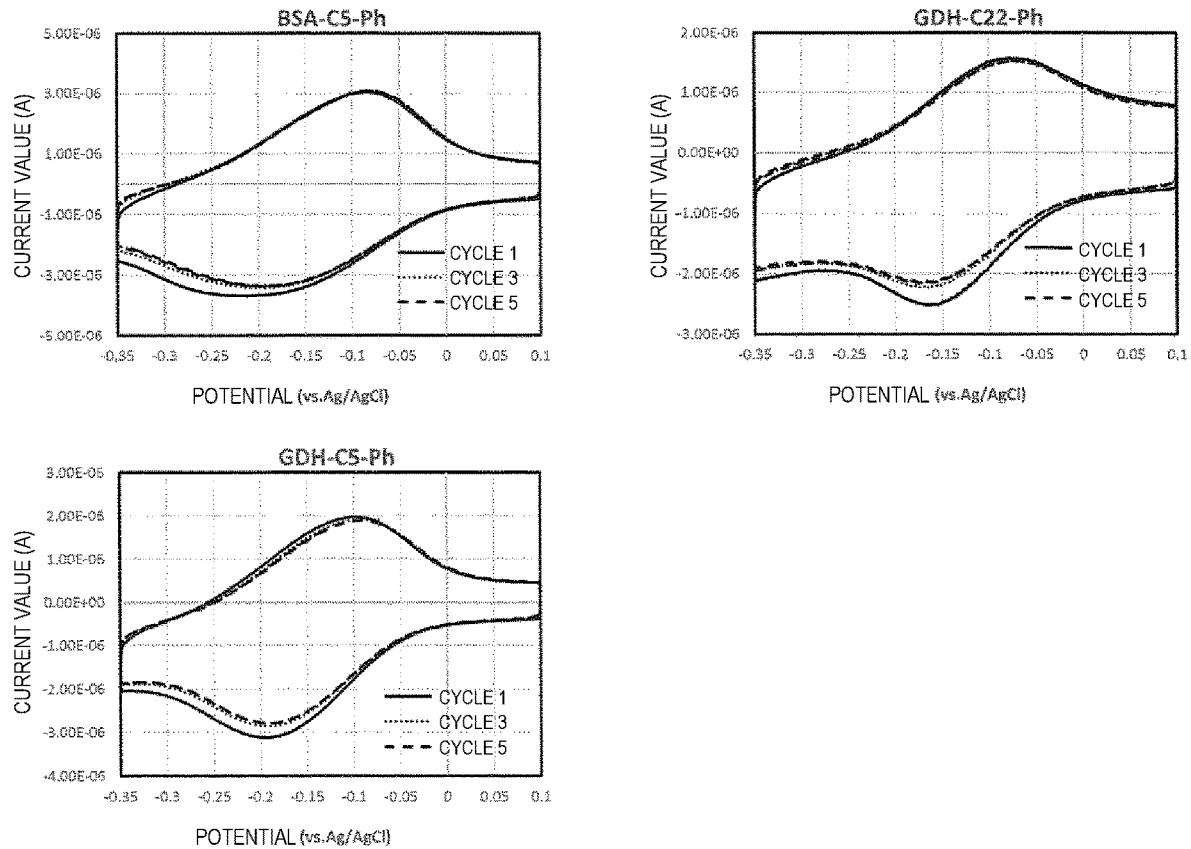
FIG. 9 is a voltammogram of the sensor of the present disclosure using a protein to which a phenazine derivative is covalently bonded.
Figure 10:
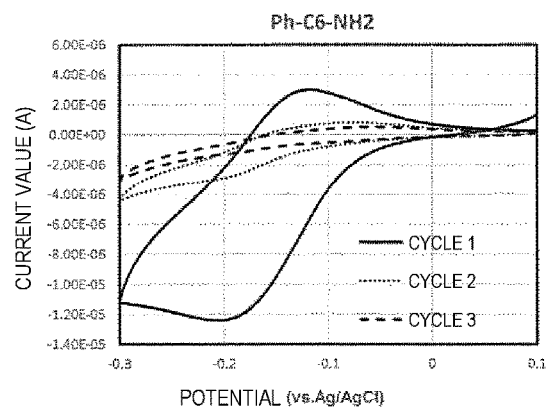
FIG. 10 is a voltammogram of a sensor using a low molecular weight phenazine derivative as a comparison.

These electrodes were immersed in PBS and made stationary at the initial potential for 10 seconds before potential sweep was initiated. The obtained cyclic voltammograms are shown in FIGS. 7 to 9.

In an electrode using the low molecular weight phenazine derivative Ph-C6-NH2 of Comparative Example 1, oxidation peaks almost disappeared during Cycle 3. In contrast, oxidation peaks were maintained beyond Cycle 3 in electrodes using the phenazine derivative-bonded high molecular weight redox polymers obtained in Examples 1 to 7 and beyond Cycle 5 in electrodes using the phenazine derivative-bonded proteins obtained in Examples 8 to 10.

These results indicate that low molecular weight phenazine derivatives leach out of the electrode, whereas leaching of phenazine derivatives out of the electrode was prevented by bonding them to the high molecular weight polymer or the protein.

(2) Mediator Preservation Stability

The absorption spectra of the high molecular weight redox polymers obtained in Examples 11 to 14 were measured at the initial stage of synthesis and after stored at 37°

Figure 11:
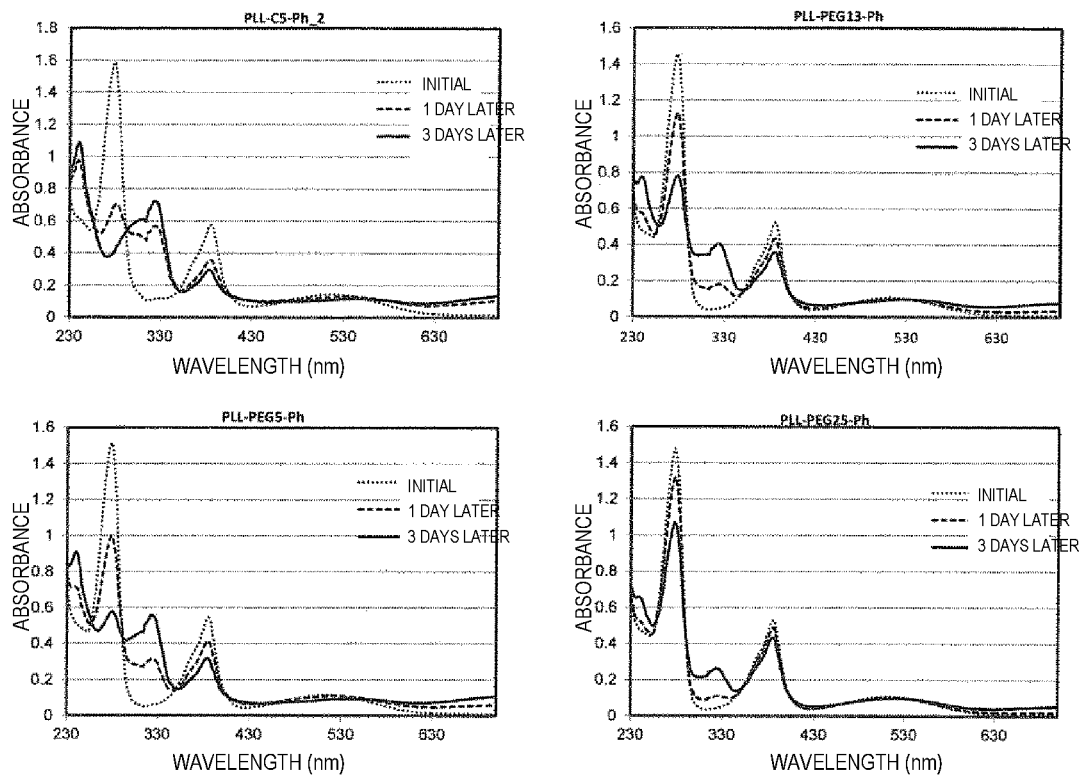
FIG. 11 shows absorption spectra of the high molecular weight polymer of the present disclosure to which a phenazine derivative is covalently bonded.

C. for one day and three days. Measurement was performed by adding 100 µL of a solution of each high molecular weight redox polymer to a microplate (Greiner Bio-One; UV-STAR MICROPALLETE 96 WELL F-BODEN) and using a plate reader (TECAN; Infinite M200 PRO). The absorbance was obtained by reducing the measured absorbance of PBS as a blank value. The obtained absorption spectra are shown in FIG. 11.

The changes in absorption peaks near 280 nm and 385 nm indicate that there are less changes in absorption peaks with a longer PEG chain, as compared with PLL-C5-Ph 2.

This result shows that the thermostability of redox mediators in a biological environment is improved by increasing the distance between the phenazine moiety and the polymer main chain.

(3) Measurement of Probe Properties

The glucose responsiveness and durability of a sensor prepared on a gold electrode with the following composition and procedure.

<Preparation of Solutions>

(a) Enzyme/Mediator Solution

A glucose dehydrogenase (FAD-dependent) (BBI International; GDH GLD1), 20% glutaraldehyde solution (Wako Pure Chemical Industries, Ltd.), and PLL-PEG25-Ph synthesized as in Example 14 were mixed to the following final concentration for each reagent, and the mixture was allowed to react for approximately 2 hours.

TABLE 1

| Reagent | Final concentration |
| --- | --- |
| GDH GLD1 | 20000 U/mL |
| PLL-PEG25-Ph | Absorbance at 386 nm equivalent to 3.1 |
| Glutaraldehyde | 0.01% |

(b) Suspension of Carbon Fine Particles

Ketjen Black EC600JD (Lion Specialty Chemicals Co., Ltd.) was suspended in Milli-Q water to a concentration of 2 mg/mL, and the suspension was treated with an ultrasonic homogenizer for 10 minutes or longer. If a few hours had passed after preparation of the suspension, the suspension was treated with the ultrasonic homogenizer again for approximately 10 minutes before use.

(c) Solution of Polymer for a Protective Film

Poly(4-vinylpyridine) (Mw=160,000) (Sigma-Aldrich) [P4VP] was dissolved in ethanol to a concentration of 10% (weight/volume) to prepare a P4VP ethanol solution.

<Preparation of Sensor>

In a volume of 0.5 µL of the ketjen black suspension was applied on the gold working electrode and dried for approximately 5 minutes. Application and drying were further repeated twice, that is, the ketjen black suspension was applied a total of three times. Zero point five µL of the enzyme/mediator solution after the reaction for 2 hours was applied and dried for approximately 30 minutes. Further, the electrode was immersed in the P4VP ethanol solution, dried for 10 minutes, then immersed again, and dried for 30 minutes or longer to form a protective film and prepare a sensor.

<Electrochemical Measurement>

Figure 12:
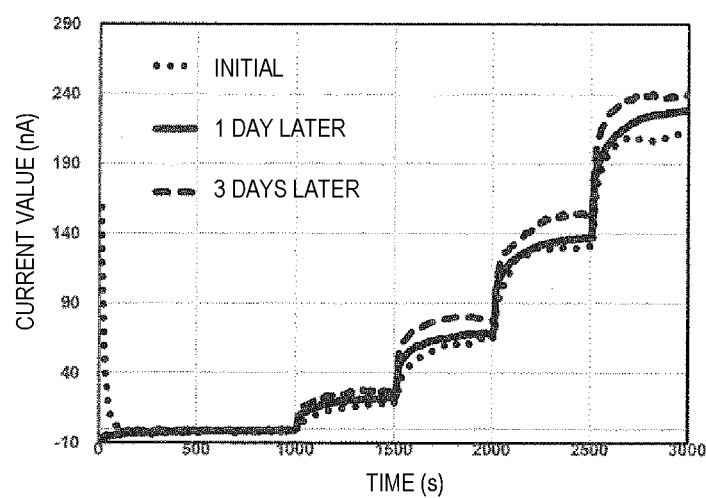
FIG. 12 is a graph showing the glucose response characteristics of a probe using the high molecular weight polymer of the present disclosure to which a phenazine derivative is covalently bonded.
Figure 13:
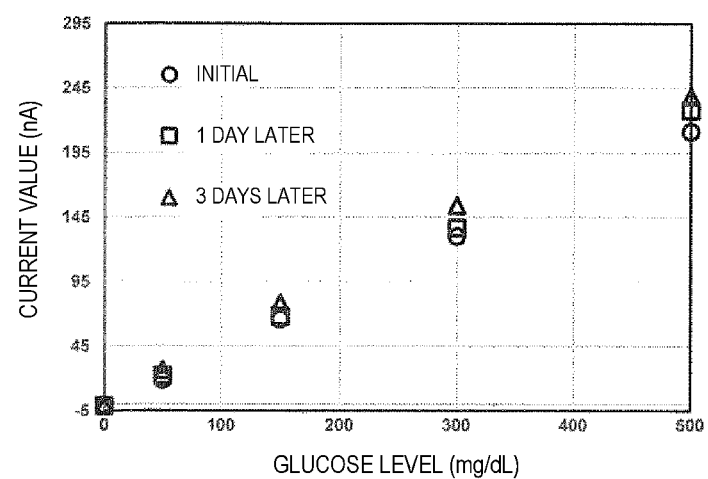
FIG. 13 is a graph showing the durability of a probe using the high molecular weight polymer of the present disclosure to which a phenazine derivative is covalently bonded.

A measurement for amperometric i-t curve was performed using a potentionstat (BAS Inc.) with three electrodes comprising the above-described sensor as a working electrode, a gold electrode as a counter electrode, and Ag/AgCl (saturated potassium chloride) (BAS Inc.) as a reference electrode while immersing the prepared sensor in PBS. Starting at 1000 seconds after the initiation of measurement, glucose was added every 500 seconds to concentrations of 50, 150, 300, and 500 mg/dL, and the current response value was continuously measured. After measurement, the sensor was preserved in PBS at 37° C., and similar measurement was performed after one day and three days of preservation. The respective measurement results are shown in FIGS. 12 and 13 and summarized in Table 2.

TABLE 2

| Amount of glucose added | Current value (nA) (nA) | | |
| --- | --- | --- | --- |
| (mg/dL) | Day 0 | Day 1 | Day 3 |
| 0 | −0.6 | −1.2 | −0.6 |
| 50 | 19.1 | 22.1 | 26.6 |
| 150 | 66.1 | 68.2 | 78.3 |
| 300 | 130.2 | 136.8 | 154.0 |
| 500 | 211.4 | 227.8 | 238.8 |

A high linearity was observed at glucose concentrations of 0 to 500 mg/dL, indicating favorable glucose responsiveness.

After preservation at 37° C. for three days, a high linearity was still observed at glucose concentrations of 0 to 500 mg/dL, and the current values did not decrease compared with the initial responses, indicating favorable durability.

INDUSTRIAL APPLICABILITY

The high molecular weight redox polymer of the present disclosure can prevent redox mediators constituting a detection layer from leaching out of the biosensor probe, while maintaining and improving responsiveness and durability, because the redox mediators are covalently bonded to the high molecular weight polymer main chain. Therefore, the high molecular weight redox polymer of the present disclosure is useful particularly for an embedded biosensor.

REFERENCE SIGNS LIST

1 Embedded electrochemical glucose sensor
10 Main body
11 Probe
111 Insulating substrate
112 Conductive thin film
112a Working electrode lead
112b Reference electrode lead
112c Counter electrode lead
113 Groove
114 Working electrode
115 Reference electrode
116 Insulating resist
117 Counter electrode
118 Detection layer
119 Protective film
2 Living body

The invention claimed is:

1. A sensor for detecting or quantifying a specimen contained in a sample, comprising at least a phenazine derivative represented by general formula (1):

[Formula 1]

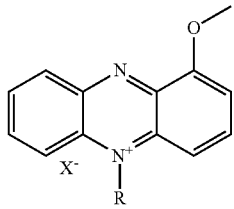
(1)

wherein X⁻ represents an anionic species, and R represents an organic group having an amino group or a carboxyl group at an end;

and a specimen-responsive enzyme.

2. The sensor according to claim 1, wherein the phenazine derivative represented by general formula (1) is a phenazine derivative represented by general formula (2):

[Formula 2]

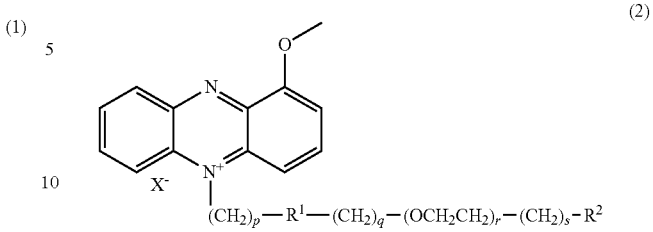
(2)

wherein X⁻ represents an anionic species; $R^1$ does not exist or is —O—, —C(=O)—NH—, or —NH—C(=O)—; $R^2$ is —COOH or —NH$_2$ or a salt thereof; p, q, and s are each independently an integer of 1 to 15; and r is an integer of 0 to 30.

3. The sensor according to claim 1, wherein the phenazine derivative represented by general formula (1) is selected from the group consisting of phenazine derivatives having an amino group represented by the following formula:

[Formula 3]

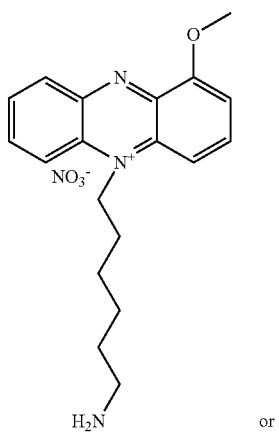

or

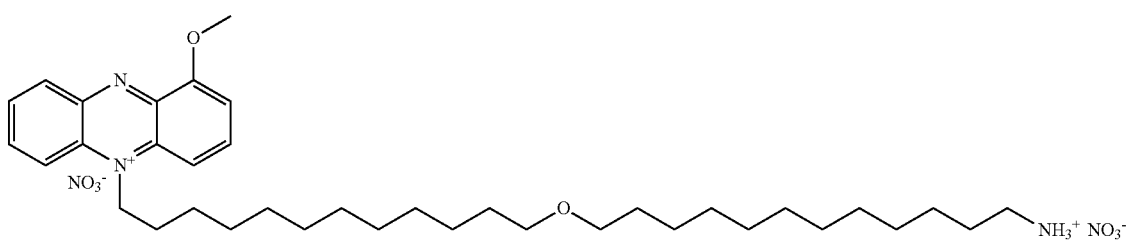

or selected from the group consisting of phenazine derivatives having a carboxyl group represented by the following formula:
[Formula 4]
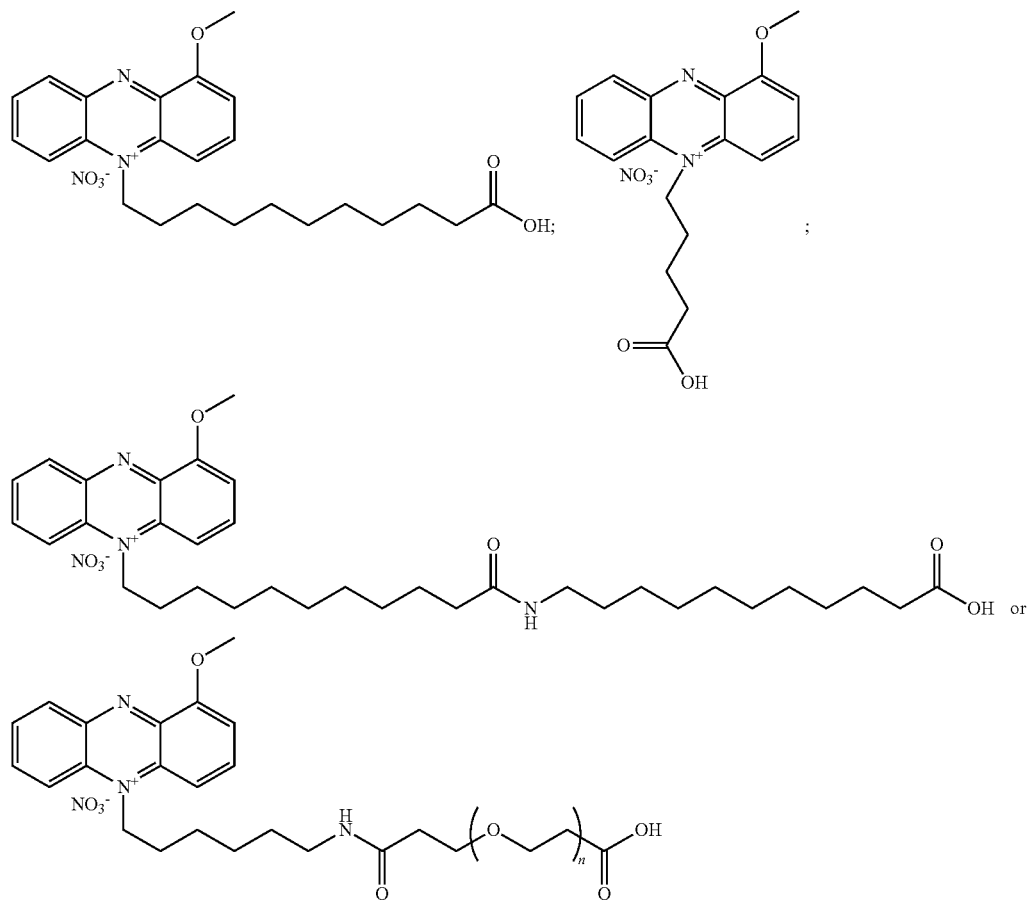
wherein n represents an integer of 1 to 30.
4. The sensor according to claim 1, wherein the specimen is glucose, and the specimen-responsive enzyme is glucose oxidase or glucose dehydrogenase.
* * * * *